(12) United States Patent
Amstutz

(10) Patent No.: US 10,739,852 B2
(45) Date of Patent: Aug. 11, 2020

(54) SYSTEMS, DEVICES, AND/OR METHODS FOR WRISTBANDS

(71) Applicant: Logan Amstutz, Kalamazoo, MI (US)

(72) Inventor: Logan Amstutz, Kalamazoo, MI (US)

(*) Notice: Subject to any disclaimer, the term of this patent is extended or adjusted under 35 U.S.C. 154(b) by 0 days.

(21) Appl. No.: 16/517,558

(22) Filed: Jul. 20, 2019

(65) Prior Publication Data

US 2020/0209964 A1 Jul. 2, 2020

Related U.S. Application Data

(63) Continuation-in-part of application No. 16/237,717, filed on Jan. 1, 2019.

(51) Int. Cl.

| | |
|---|---|
| *G06F 3/01* | (2006.01) |
| *G06F 3/038* | (2013.01) |
| *G06F 3/16* | (2006.01) |
| *G06K 9/00* | (2006.01) |
| *A61B 5/024* | (2006.01) |
| *A61B 5/00* | (2006.01) |
| *G08B 21/22* | (2006.01) |

(52) U.S. Cl.
CPC .......... *G06F 3/014* (2013.01); *A61B 5/02438* (2013.01); *A61B 5/681* (2013.01); *G06F 3/038* (2013.01); *G06F 3/167* (2013.01); *G06K 9/00402* (2013.01); *G08B 21/22* (2013.01); *G06F 2203/0331* (2013.01); *G06K 9/00624* (2013.01)

(58) Field of Classification Search
CPC .......... G06F 3/014; G06F 3/167; G06F 3/038; G06F 2203/0331; G06K 9/00402; G06K 9/00624; G08B 21/22; A61B 5/02438; A61B 5/681
See application file for complete search history.

(56) References Cited

U.S. PATENT DOCUMENTS

| | | | | |
|---|---|---|---|---|
| 2015/0100323 | A1* | 4/2015 | Kozuka | G06F 3/017 704/275 |
| 2015/0370320 | A1* | 12/2015 | Connor | A61B 5/6831 345/173 |
| 2015/0378447 | A1* | 12/2015 | Nagano | G06F 1/1626 700/85 |

* cited by examiner

*Primary Examiner* — Mark W Regn
(74) *Attorney, Agent, or Firm* — Dale Jensen, PLC; Dale Jensen

(57) ABSTRACT

Certain exemplary embodiments can provide an attachment coupled to a hand of a user. The attachment can comprise a laser sensor. The attachment can be constructed to cause a signal to be transmitted via the wireless transmitter responsive to motion of a finger of the user determined by the laser sensor. The attachment can comprise wireless transceiver.

7 Claims, 6 Drawing Sheets

SYSTEMS, DEVICES, AND/OR METHODS FOR WRISTBANDS

CROSS-REFERENCES TO RELATED APPLICATIONS

This application is a continuation-in-part of, and incorporates by reference herein in its entirety, pending U.S. patent application Ser. No. 16/237,717, filed Jan. 1, 2019.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Certain exemplary embodiments can provide an attachment coupled to a hand of a user. The attachment can comprise a laser sensor. The attachment can be constructed to cause a signal to be transmitted via the wireless transmitter responsive to motion of a finger of the user determined by the laser sensor. The attachment can comprise wireless transceiver.

Figure 1:
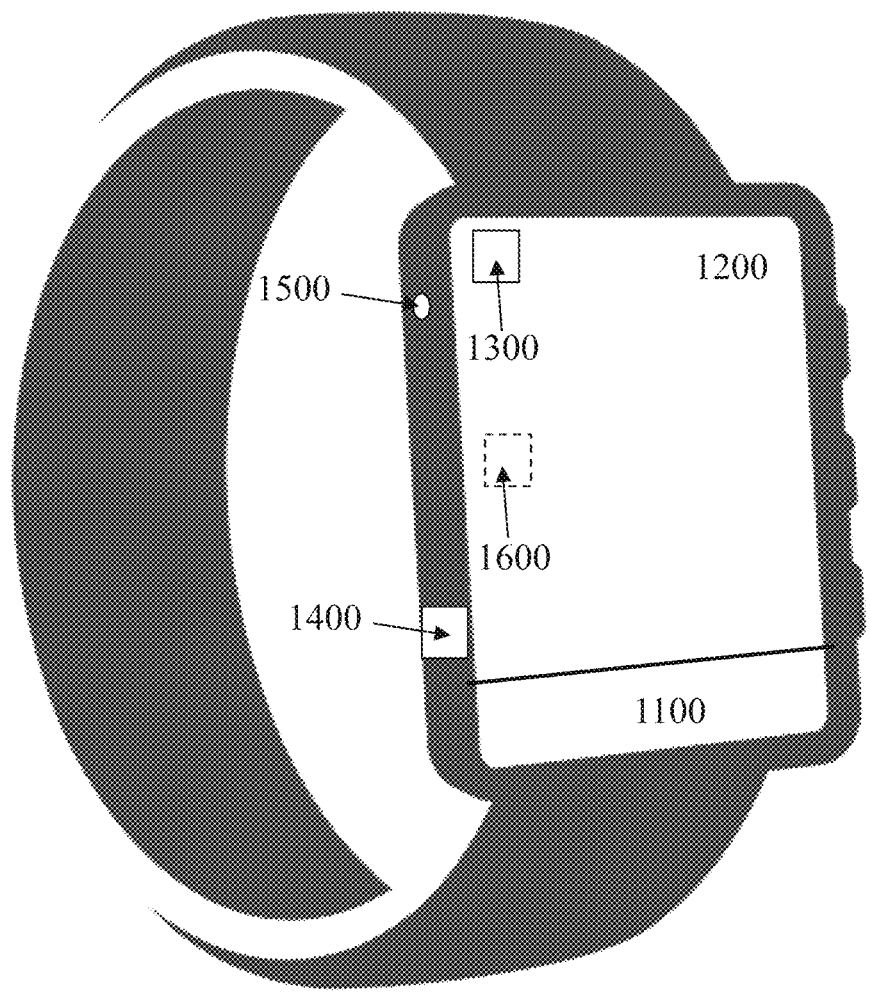
FIG. 1 is a side view of an exemplary embodiment of a wristband 1000.

FIG. 1 is a side view of an exemplary embodiment of a wristband 1000. Wristband can be constructed, via a wireless transceiver 1300, to receive signals from an attachment (see, e.g., finger attachment 3000 of FIG. 3). Wristband 1000 can be constructed to analyze signals from the attachment to determine that characters are being written by the user. Wristband 1000 can be constructed to cause an audio of characters written by the user to be played by a speaker/microphone 1400 or to an earpiece port 1500.

Via speech recognition methods, wristband 1000 is constructed to receive audio inputs from the user that assist wristband 1000 in machine learning of characters indicated by motion of the finger of the user. Certain exemplary embodiments can utilize algorithms to recognize characters based upon the wearing user's handwriting and algorithms that use heuristic rules to parse the handwritten characters into words and phrases. For example, one or more methods such as is disclosed in U.S. Pat. No. 7,724,957, which is incorporated by reference herein in its entirety, can be used.

Via speech recognition methods, wristband 1000 is constructed to receive audio inputs from the user that assist wristband 1000 in determining that no characters have been indicated by motion of the finger of the user. Wristband 1000 can be constructed to transmit signals indicative of writing to a server via a network. Responsive to a user selection, the server can cause writings of the user to be uploaded to a website.

Wristband 1000 can comprise a cardiac monitor 1600 that is constructed to monitor a heart rate of the user. Wristband 1000 can be constructed to determine a room of a structure responsive to an analysis of the heart rate of the user. Wristband 1000 can be constructed to render a color of a plurality of colors, each of color representing the determined location in the structure.

In certain exemplary embodiments, a predetermined letter can be highlighted, illuminated, and/or rendered responsive to a heart rate exceeding a predetermined threshold.

Figure 2:
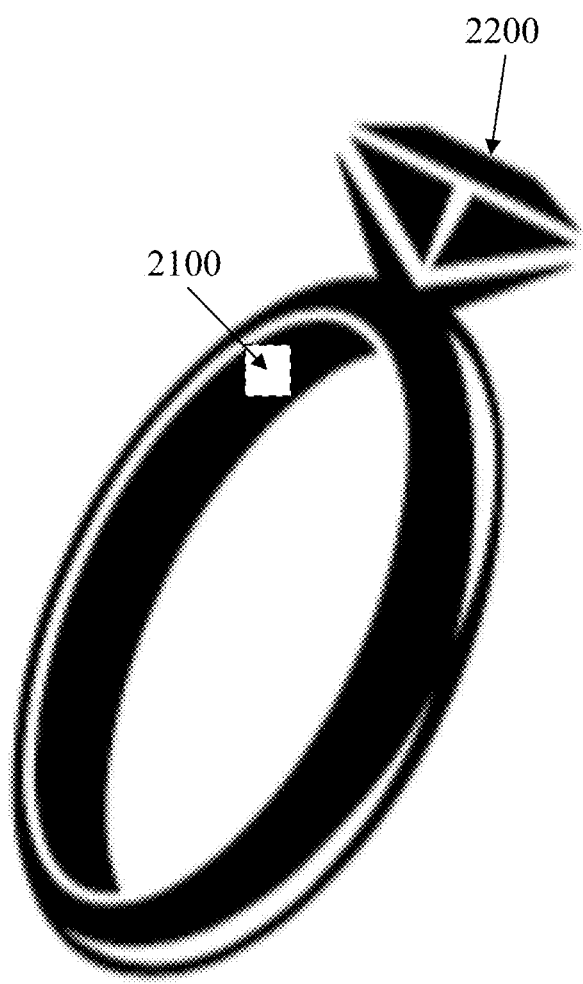
FIG. 2 is a side view of an exemplary embodiment of a ring 2000.

FIG. 2 is a side view of an exemplary embodiment of a ring 2000. Ring 2000 can comprise a camera 2200. Ring 2000 comprises a wireless transceiver 2100 constructed to transmit images. A wristband (e.g., wristband 1000 of FIG. 1) is constructed to determine a room of a structure responsive to images transmitted by the ring. The wristband can be constructed to render a color of a plurality of colors, each of color representing the determined location in the structure.

The wristband (e.g., wristband 1000 of FIG. 1) can be constructed to determine another person is in proximity of the user based upon transmitted images. The wristband can be constructed to render an alert to the user concerning proximity of another person detected via camera 2200. The wristband can be constructed to analyze the images to determine one or more characteristics of each image. The wristband can be constructed to render the one or more characteristics of each image.

Certain exemplary embodiments provide a body camera (see, e.g., body camera 3800 of FIG. 3A) comprising a wireless transceiver (see, e.g., wireless transceiver 3900 of FIG. 3A) constructed to transmit images. The wristband can be constructed to analyze the images to determine one or more characteristics of each image. The wristband can render the one or more characteristics of each image.

Certain exemplary embodiments provide a wristband, which comprises an information device. The wristband comprises hardware and/or software constructed to perform one or more of the following functions:
  monitor one or more cardiac functions, such as heart rate;
  determine a location in or outside of a structure (e.g., a particular room such as a bedroom, bathroom, basement, living room, kitchen, and/or outdoor location, etc.) responsive to an analysis of the one or more monitored cardiac functions;
  render a color of a plurality of colors, each of color representing the determined location in the structure; etc.

Figure 3:
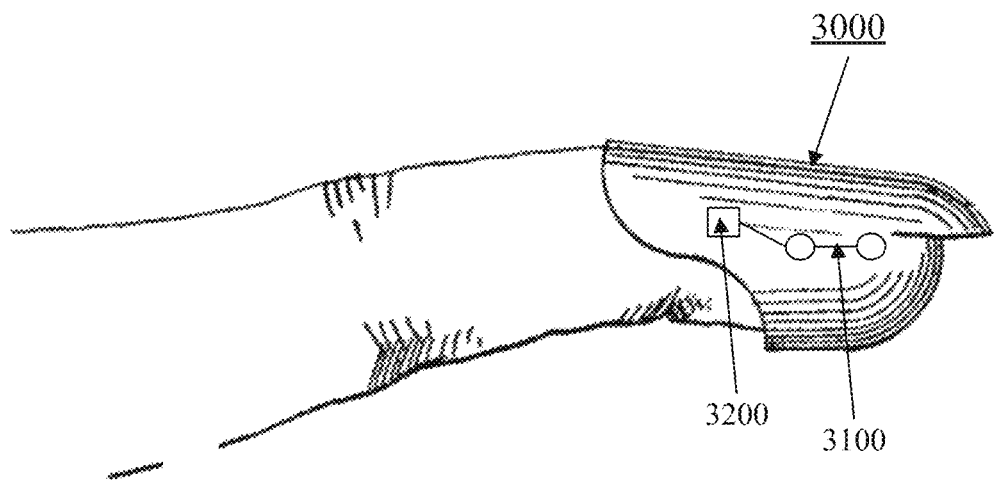
FIG. 3 is a sketch of a view of an exemplary embodiment of a finger attachment 3000.

FIG. 3 is a sketch of a view of an exemplary embodiment of a finger attachment 3000. Finger attachment 3000 can be constructed to interact with a touch sensitive surface. In certain exemplary embodiments, finger attachment 3000 comprises an electronic sensor system 3100, which detects finger movement. Signals indicative of finger movement can be transmitted via a wireless transmitter 3200 to an information device for processing.

Certain exemplary embodiments provide an attachment coupled to a hand of a user, the attachment comprising a laser sensor, the attachment constructed to cause a signal to be transmitted via the wireless transmitter responsive to motion of a finger of the user determined by the laser sensor, the attachment comprising wireless transceiver.

In certain exemplary embodiments, finger attachment 3000 can trigger a recordation of audio through a speaker/microphone (e.g., speaker/microphone 1400 of FIG. 1). In certain exemplary embodiments cause the speaker/microphone to ask a user for information concerning finger movement (e.g., the speaker/microphone can ask a question such as "did you just write an "r"?, or "please spell out what your wrote"?) and a response can be received via the speaker/microphone. An information device comprised by the wristband, or communicatively coupled to the wristband, can compare responses of the user to programmed choices of characters and/or writing. Thereby, machine learning can be facilitated.

Certain exemplary embodiments can suggest completion of phrases based upon an initial detected character, word, or phrase written by the user. The completion of phrases suggestions can be rendered on a user interface of the wristband. A touch sensitive surface comprised by the wristband can receive a touch input by the user accepting one or more of the suggested completion of phrases. For example, if a user writes "Trisha is so awesome no one wants to say it aloud", the information device comprised by and/or coupled to the wristband can suggest a phrase the next time the name "Trisha" is detected. For example, a suggestion of "is my friend" might be the suggested completion of phrases.

In certain exemplary embodiments, audio can be triggered via finger attachment 3000 detecting a relaxation of a hand of the user.

Figure 3A:
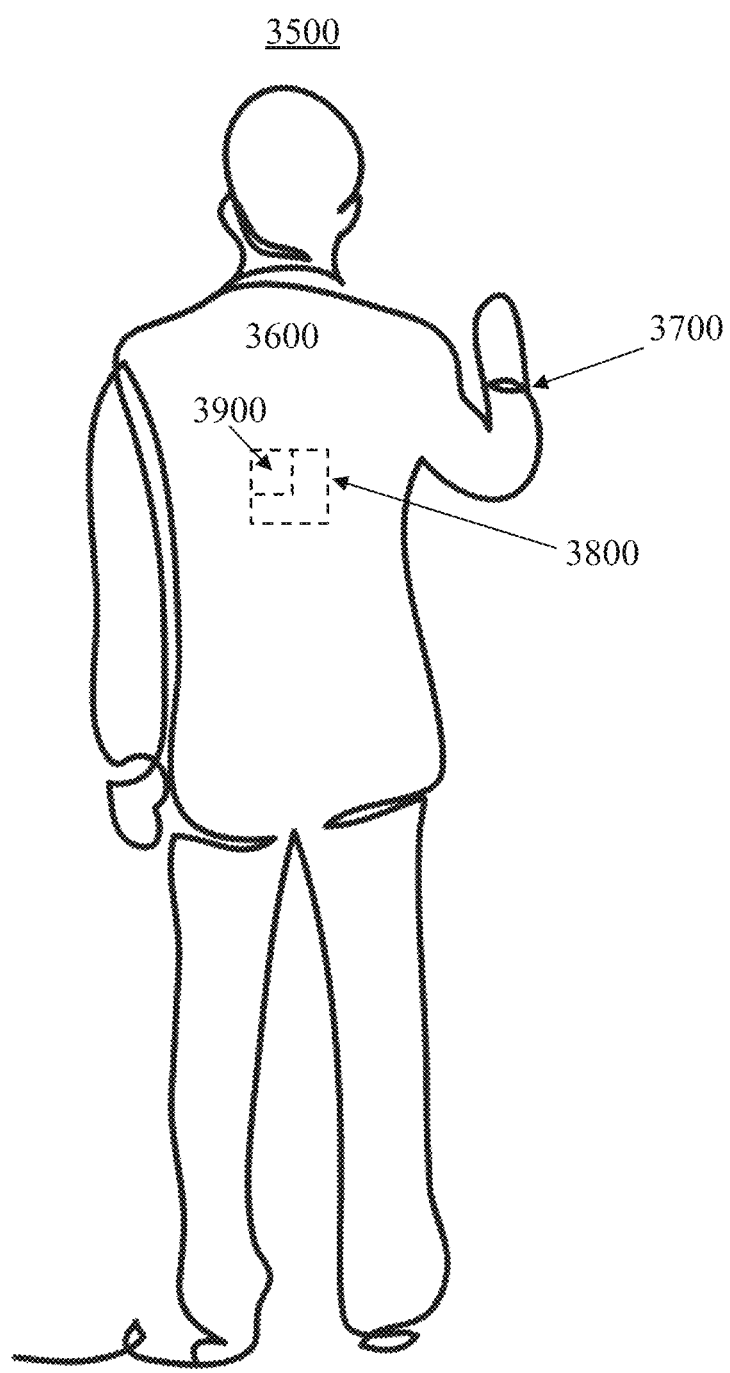
FIG. 3A is a block diagram of an exemplary embodiment of a system 3500.

FIG. 3A is a block diagram of an exemplary embodiment of a system 3500, which comprises a human 3600, a wristband 3700, and a body camera 3800. Body camera 3800 comprises a wireless transceiver 3900.

Figure 4:
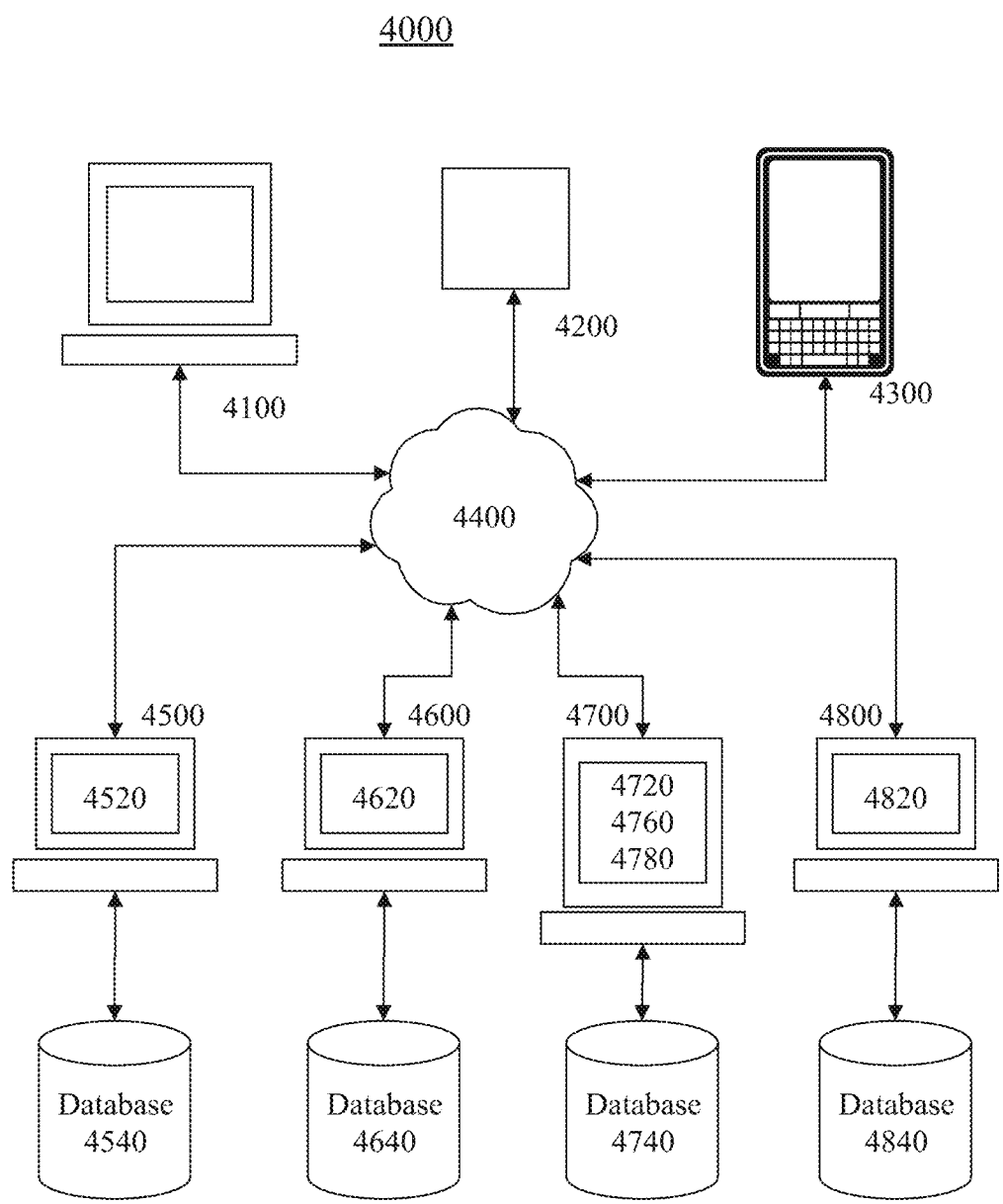
FIG. 4 is a block diagram of an exemplary embodiment of a system 4000.

FIG. 4 is a block diagram of an exemplary embodiment of a system 4000, which can comprise a smartphone 4300, an information device 4100, tablet 4200, a network 4400, a first server 4500, a second server 4600, a third server 4700, and a fourth server 4800. First server 4500 can comprise a first user interface 4520 and can be coupled to a first database 4540. Second server 4600 can comprise a second user interface 4620 and can be coupled to a second database 4640. Third server 4700 can comprise a third user interface 4720, a processor 4760, machine instructions 4780, and can be coupled to a third database 4740. Fourth server 4800 can comprise a fourth user interface 4820 and can be coupled to a fourth database 4840. Any of the methods and/or steps thereof can be carried out in whole or in part by tablet 4200, smartphone 4300, information device 4100 and/or first server 4500. Second server 4600, third server 4700, and/or fourth server 4800 can each be associated with implementation of a system via which facilitates communication of a user utilizing a finger pointer that is communicatively coupled to a band that can be worn around a wrist of a user. In certain exemplary embodiments, system 4000 can be used to implement one or more methods disclosed herein.

Figure 5:
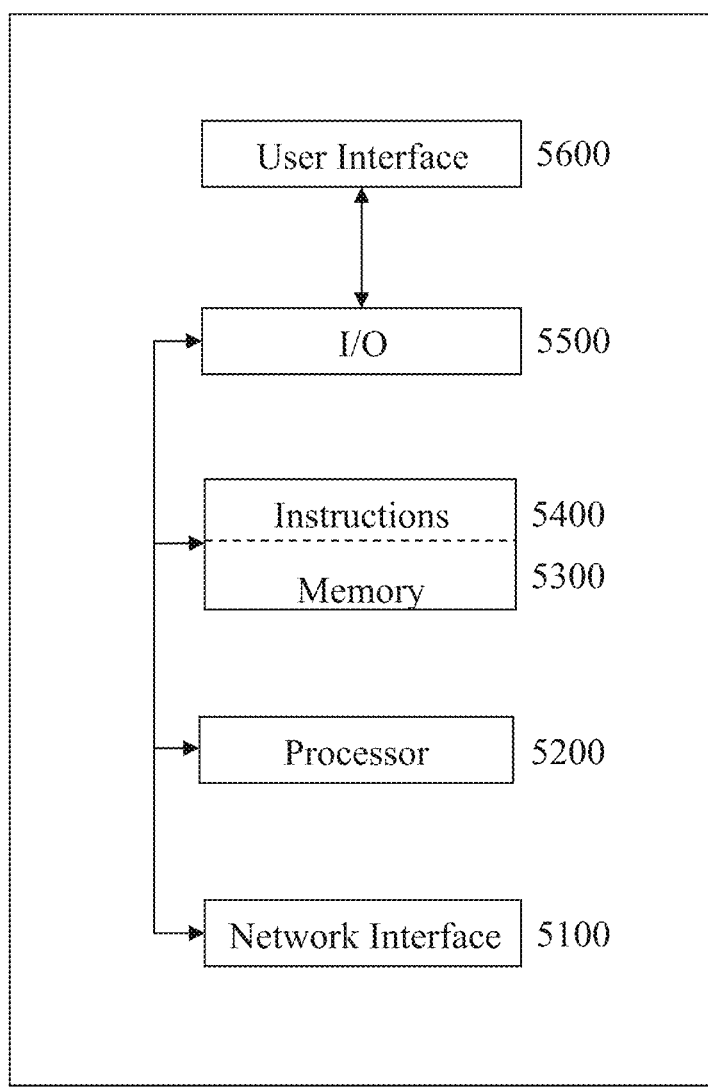
FIG. 5 is a block diagram of an exemplary embodiment of an information device 5000.

FIG. 5 is a block diagram of an exemplary embodiment of an information device 5000, which in certain operative embodiments can comprise, for example, first server 4500, and/or user information device 4100, of FIG. 4. Information device 5000 can comprise any of numerous circuits and/or components, such as for example, one or more network interfaces 5100, one or more processors 5200, one or more memories 5300 containing instructions 5400, one or more input/output devices 5500, and/or one or more user interfaces 5600 coupled to one or more input/output devices 5500, etc.

In certain exemplary embodiments, via one or more user interfaces 5600, such as a graphical user interface, a user can view a rendering of information related to a user communicating with an information device.

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, step, and/or process or portion thereof adapter—a device used to effect operative compatibility between different parts of one or more pieces of an apparatus or system.

alert—an electrical, electronic, or mechanical device and/or display that serves to advise of a condition by means of a sound or signal.

analyze—evaluate.

and/or—either in conjunction with or in alternative to.

apparatus—an appliance or device for a particular purpose associate—to join, connect together, and/or relate.

attachment—a coupled device.

audio—a noise that can be heard by a human or animal.

automatically—acting or operating in a manner essentially independent of external influence or control. For example, an automatic light switch can turn on upon "seeing" a person in its view, without the person manually operating the light switch.

camera—an instrument constructed to record and/or capture still and/or moving images.

can—is capable of, in at least some embodiments.

cardiac monitor—continuous or intermittent monitoring of heart activity.

character—a graphic symbol (such as an alphabet letter) used in writing.

characteristic—a defining feature.

circuit—an electrically conductive pathway and/or a communications connection established across two or more switching devices comprised by a network and between corresponding end systems connected to, but not comprised by the network.

close—covering a compartment.

color—a characteristic of human visual perception described through color categories, with names such as red, yellow, purple, or blue.

compartment—a partitioned space.

comprising—including but not limited to.

configure—to make suitable or fit for a specific use or situation.

connect—to join or fasten together.

constructed to—made to and/or designed to.

convert—to transform, adapt, and/or change.

couple—to link in some fashion.

coupleable—capable of being joined, connected, and/or linked together.

cover—a thing that lies on or over an compartment in order to control ingress and/or egress of objects via the compartment.

data—distinct pieces of information, usually formatted in a special or predetermined way and/or organized to express concepts.

define—to establish the outline, form, or structure of determine—to obtain, calculate, decide, deduce, and/or ascertain.

device—a machine, manufacture, and/or collection thereof.

earpiece—a device that is placed against or inserted into the outer opening of the ear that transmits sounds.

generate—to create, produce, give rise to, and/or bring into existence.

glove—a shaped hand covering.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

indicative—signifying.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

input—a signal, data, and/or information provided to a processor.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

install—to connect or set in position and prepare for use.

laser—a device that generates an intense beam of coherent monochromatic light (or other electromagnetic radiation) by stimulated emission of photons from excited atoms or molecules.

location—a place substantially approximating where something physically exists.

machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine learning—algorithms information devices use in order to perform a specific task effectively without using explicit instructions, relying on patterns and inference instead. It is seen as a form of artificial intelligence.

machine readable medium—a physical structure from which a machine can obtain data and/or information. Examples include a memory, punch cards, etc.

manner—a way of doing.

may—is allowed and/or permitted to, in at least some embodiments.

medical provider—an individual or institution that treats patient maladies.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

monitor—to keep track of.

motion—a process via which something changes position from one location to another.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

open—allowing access to inside.

packet—a discrete instance of communication.

play—to emit sounds.

plurality—the state of being plural and/or more than one.

port—an opening constructed to receive a plug.

predetermined—established in advance.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

project—to calculate, estimate, or predict.

provide—to furnish, supply, give, and/or make available.

receive—to get as a signal, take, acquire, and/or obtain.

recommend—to suggest, praise, commend, and/or endorse.

record—to set down in some tangible form (e.g., write on a paper) for later reference.

remove—to take something out of a space (e.g., to take something out of a compartment).

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker/microphone, etc.

repeatedly—again and again; repetitively.

request—to express a desire for and/or ask for.

responsive—reacting to an influence and/or impetus.

ring—a band of material constructed to be worn on a human finger and constructed to perform one or more predetermined functions.

room—a part of a building.

sense—to detect or perceive automatically.

sensitive—able to sense.

sensor—a device used to measure a physical quantity (e.g., temperature, pressure, capacitance, and/or loudness, etc.) and convert that physical quantity into a signal of some kind (e.g., voltage, current, power, etc.). A sensor can be any instrument such as, for example, any instrument measuring pressure, temperature, flow, mass, heat, light, sound, humidity, proximity, position, velocity, vibration, voltage, current, capacitance, resistance, inductance, and/or electro-magnetic radiation, etc. Such instruments can comprise, for example, proximity switches, photo sensors, thermocouples, level indicating devices, speed sensors, electrical voltage indicators, electrical current indicators, on/off indicators, and/or flowmeters, etc.

set—a related plurality.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

speaker/microphone—an electroacoustic device that emits sounds from an input signal, which sounds are audible to a human.

speech recognition—the ability of a computer to identify and respond to the sounds produced in human speech.

store—to place, hold, and/or retain data, typically in a memory.

structure—a building.

stylus—a device constructed to input commands, handwritten text, and/or drawings, etc.

substantially—to a great extent or degree.

support—to bear the weight of, especially from below.

surface—the outer boundary of an object or a material layer.

system—a collection of mechanisms, devices, machines, articles of manufacture, processes, data, and/or instructions, the collection designed to perform one or more specific functions.

touch—to contact something.

transmit—to send as a signal, provide, furnish, and/or supply.

transparent—allowing light to pass through so that objects behind can be distinctly seen with a human eye.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker/microphone, microphone, and/or other sound generating and/or receiving device. A video element or animation element can be provided, for example, via a monitor, display, projector, and/or other visual device. A haptic element can be provided, for example, via a very low frequency speaker/microphone, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

via—by way of and/or utilizing.

website—machine instructions addressable via the Internet, which cause rendering of one or more browser pages on the World Wide Web.

wireless transceiver—a device constructed to transfer signals between sources and destinations without the use of wires.

wireless transmitter—a device constructed to transfer a signal from a source to a destination without the use of wires.

wristband—a strap that couples to a human wrist and performs a set of functions (e.g., a smartwatch).

writing—a medium of human communication in which information is conveyed via recorded signs and symbols.

written—conveyed via writing.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A system comprising:
an attachment coupled to a hand of a user, the attachment comprising a laser sensor, the attachment constructed to cause a first signal to be transmitted via a first wireless transmitter responsive to motion of a finger of the user determined by the laser sensor, the attachment comprising wireless transceiver;
a wristband, the wristband constructed to receive the first signal from the attachment, the wristband constructed to analyze the first signal from the attachment to determine that characters are being written by the user, the wristband constructed to cause an audio of characters written by the user to be played by a speaker/microphone or to an earpiece port; wherein
the wristband comprises a cardiac monitor that is constructed to monitor a heart rate of the user;
the wristband is constructed to determine a room of a structure responsive to an analysis of the heart rate of the user; and
the wristband is constructed to render a color of a plurality of colors, the color indicating the determined room in the structure.

2. The system of claim 1, wherein:
via speech recognition methods, the wristband is constructed to receive audio inputs from the user that assist the wristband in machine learning of characters indicated by motion of the finger of the user.

3. The system of claim 1, wherein:
via speech recognition methods, the wristband is constructed to receive audio inputs from the user that assist the wristband in determining that no characters have been indicated by motion of the finger of the user.

4. The system of claim 1, wherein:
the wristband is constructed to transmit a second signal indicative of writing to a server via a network; and
responsive to a user selection, the server causes writings of the user to be uploaded to a website.

5. The system of claim 1, wherein:
a ring, the ring comprising a camera, the ring comprising a second wireless transmitter constructed to transmit images;
the wristband is constructed to determine a room of a structure responsive to images transmitted by the ring; and
the wristband is constructed to render a color of a plurality of colors, the color indicating the determined room in the structure.

6. The system of claim 1, wherein:
a ring, the ring comprising a camera, the ring comprising a second wireless transmitter constructed to transmit images;
the wristband is constructed to determine another person is in proximity of the user; and
the wristband is constructed to render an alert to the user concerning proximity of another person.

7. The system of claim 1, further comprising:
a ring, the ring comprising a camera, the ring comprising a second wireless transmitter constructed to transmit images; and
the wristband is constructed to analyze the images to determine one or more characteristics of each image; and
the one or more characteristics of each image is rendered via the wristband.

* * * * *